United States Patent [19]

Curtis et al.

[11] Patent Number: 4,965,430
[45] Date of Patent: Oct. 23, 1990

[54] METHOD OF LASER MACHINING MOLDS WITH MICROTEXTURED SURFACES

[75] Inventors: James M. Curtis, Bartlett, Tenn.; Ronald S. Sanders, Eden Prairie, Minn.

[73] Assignees: Dow Corning Wright Corp., Arlington, Tenn.; Lumonics Material Processing Corporation, Eden Prairie, Minn.

[21] Appl. No.: 408,847

[22] Filed: Sep. 18, 1989

[51] Int. Cl.⁵ ............................................. B23K 26/00
[52] U.S. Cl. ........................... 219/121.69; 219/121.78; 219/121.8; 219/121.82
[58] Field of Search ....................... 219/121.68, 121.69, 219/121.78, 121.8, 121.82; 128/303.1

[56] References Cited

U.S. PATENT DOCUMENTS

| | | | |
|---|---|---|---|
| 4,455,893 | 6/1984 | Asterö | 219/121.65 X |
| 4,555,610 | 11/1985 | Polaid et al. | 219/121 LA |
| 4,729,766 | 3/1988 | Bergentz et al. | 219/121.69 X |

OTHER PUBLICATIONS

Changes in the Subcutaneous Tissue Response Caused by Implant Compliance and Surface Morphology, Elizabeth Ann Powell, Case Western Reserve Univ., May, 1982, Thesis (Spec. P2).
Master's thesis by Elizabeth Ann Powell, Case Western Reserve University, Cleveland, Ohio, entitled "Changes in the Subcutaneous Tissue Response Caused by Implant Compliance and Surface Morphology" (May 1982).

Primary Examiner—C. L. Albritton
Attorney, Agent, or Firm—Allan O. Maki

[57] ABSTRACT

A process is provided for preparing a three dimensional object such as a mandrel for forming envelopes for mammary prostheses or other implantable medical device by dipping the mandrel, etc. The envelopes are provided with micropillars on the exterior surface which resembles the mandrel surface in negative relief. According to the process a workpiece of solid stock material such as polymer is provided in the shape of the desired prostheses. It is positioned for rotation on a supporting shaft or other holding mechanism. A pulsing laser beam, directed at the workpiece is moved in a plane parallel to the axis of rotation of the workpiece while the beam is maintained approximately perpendicular to the workpiece surface. The rate of pulsing of the laser beam and the speed of rotation of the workpiece are controlled to produce patterns of blind micro-holes onthe surface of the workpiece. A noncircular pattern can be produced by oscillating the beam toward and away from the axis of rotation with each revolution of the workpiece.

8 Claims, 3 Drawing Sheets

METHOD OF LASER MACHINING MOLDS WITH MICROTEXTURED SURFACES

BACKGROUND OF THE INVENTION

1. Field of the Invention

This invention relates to a process for laser drilling blind micro-holes into the surface of a mold or mandrel which can be used to produce shaped articles such as medical devices having a micropillared textured surface thereon. In a more specific embodiment the invention relates to such a process for producing mandrels for formation of micropillared envelopes for mammary prostheses.

2. Prior Art

Laser machining has been employed for various cutting or burning procedures. Computer numerical control (CNC) systems have also been provided to control the motion of such machining systems. See, for example, Polad et al. U.S. Pat. 4,555,610 issued Nov. 26, 1985. Pulsing laser beams controlled by such systems has also heretofore been employed for altering the surfaces of articles, for example, inking rollers.

It has heretofore been proposed that mammary prostheses be constructed which have micropillars on the surface thereof for the purpose of modifying the response of tissue to the prosthesis and possibly reducing the incidence or severity of capsular contracture by the body tissues around such prostheses. Heretofore it has been proposed to form two dimensional, i.e., flat mold surfaces having blind microholes by ion beam thruster bombardment of a surface through sputter-resistant screens or masks in order to cause erosion of the target material at locations corresponding with the openings in the sputter mask or screen. The target material was then, used as a mold surface onto which a silicone or other elastomer was cast to form flat sheets with a micropillared surfaces for lamination onto a three dimensional prosthesis. See Powell E., "Changes in Subcutaneous Tissue Response caused by Implant Compliance and Surface Morphology." Masters Thesis. Case Western Reserve University Cleveland, Ohio, May 1982. Such methods have heretofore enabled construction of a small numbers of implants for experimental purposes but have not resulted in commercial production of prostheses, primarily due to the limitations of the manufacturing process which requires a lamination or bonding step.

SUMMARY OF THE INVENTION

The present invention thus meets a need for a commercially practical method of producing three-dimensional mandrels which can be used to prepare a number of envelopes for mammary prostheses or other medical devices such as bladders for left ventricle assist devices. The process of the invention involves providing a workpiece having a solid surface, for example, a rigid polymeric material which has been formed into the approximate shape or outline of the desired medical device or prosthesis. This workpiece which may be either solid throughout or hollow is positioned for rotation preferably about a selected axis of the workpiece on a supporting chuck which may be part of a laser-machining system, for example, of the general type disclosed in the Polad, et al patent. A pulsing laser beam is then directed at. the workpiece as it rotates. The laser beam is moved along the surface of the workpiece in a plane parallel to the axis of rotation of the workpiece and is at the same time maintained at a orientation approximately perpendicular to the surface of the workpiece at which the beam is pointing at any given time. The rate of pulsing of the laser beam and the speed of rotation of the workpiece are then controlled to produce desired patterns of blind micro-holes on the surface of the workpiece. The diameter and depth of the holes are determined by the laser optics and the strength and time of impact on the workpiece surface of the laser beam. The spacing between the micro-holes is controlled, as noted, by the pulsing rate of the beam and the speed of rotation, or other relative movement, between the beam and the workpiece.

DETAILED DESCRIPTION

Figure 1:
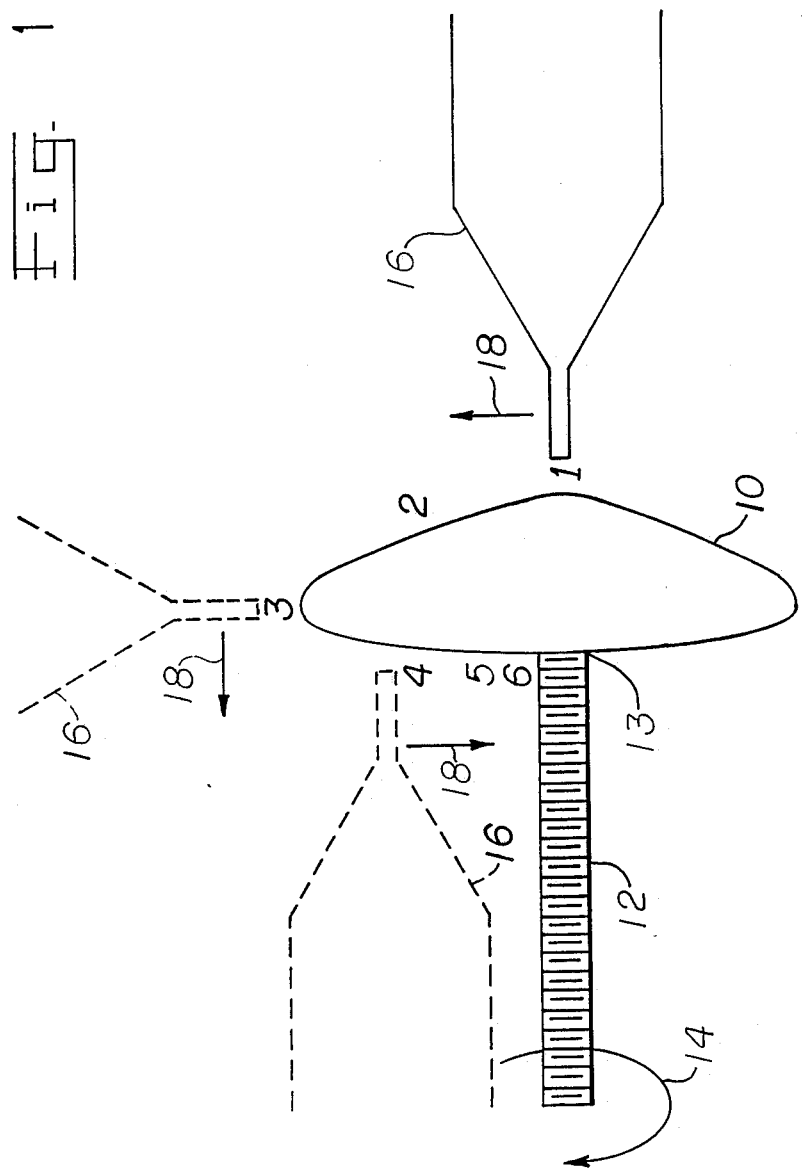
FIG. 1 is a diagrammatic view illustrating a preferred method of the present invention.

Referring more specifically to the drawings, Numeral 10 generally indicates a mandrel intended for use as a mold for formation of envelopes for mammary prostheses. Such prostheses are ultimately formed by dipping mandrel 10 into a dispersion containing a curable elastomer or by spraying or otherwise applying the dispersion to the mandrel. Mandrel 10 is supported for rotation at a point on its central axis by a holding mechanism or supporting chuck 12, the direction rotation being indicated by arrow 14. An opening at the rear center of the mandrel 10 may be provided and is commonly referred to as a stud hole 13. Stud hole 13 provides a convenient connection point for holding mechanism 12.

Numeral 16 indicates a laser beam discharge nozzle, or beam directing component, of the type disclosed in the aforesaid Polad, et al patent, the disclosure of which is incorporated herein by reference. The beam directing component 16 represents a means for delivering a focused laser beam to a workpiece, in this case mandrel workpiece 10. The directing nozzle 16 is coupled by means of an optical path to the laser. The optical path preferably includes at least 3 optical path means oriented along three different axes for extension and retraction along the axes pursuant to command signals so that the laser beam directing component can be moved in accordance with an electronically controlled program. Means are also provided to control the intensity of the laser beam as well as the speed or frequency of pulsation thereof. Likewise variable control means is provided for accurately varying the speed of rotation 14 of a holding mechanism 12, beam directing component 16 can be moved along the perimeter of workpiece 10 as indicated by arrow 18. Numerals 1-6. inclusive indicate positions at which the beam directing component may be located at different times during the course of such path. Each pulse of the laser discharged through laser beam directing component 16 will cause the drilling of a blind micro-hole in the surface of mandrel 10. The depth of hole drilled is affected by the laser energy supplied. This energy is related to the pulse width and laser power. The latter varies in a non-linear fashion with the pulse rate. Due to rotation of mandrel 10 the speed of the surface of the mandrel at location 3 is considerably more than that at location 1. Thus in order to drill at a uniform hole depth it is necessary to vary either the power or pulse width. Also, in order to drill uniform holes the laser beam must be precisely aimed at the mandrel surface. The preferred material of construction of mandrels 10 is a polymeric material such as a polyacetal, polyvinylidene fluoride, or polyethylene terephthalate. The beam-directing apparatus generally senses distance from the workpiece by capacitance. However, since the preferred mandrels are non conductive materials, it is necessary to program movement of the beam directing component based on the dimensions of the plastic mandrel without benefit of such capacitance-determined distances. Such programming can be mathematically determined based on the dimensions of the mandrel or visually determined by moving the beam directing component around the mandrel in steps which are programmed into the memory of a CNC computer control. This also may be done, if desired, using a metal mandrel having the same shape and dimensions as the desired plastic mandrel, thus permitting the use of capacitance to determine distance of the nozzle from the mandrel on each step of the movements necessary to program the CNC.

Assuming that the beam directing component is moved in the direction indicated in FIG. 1, it will be seen that the laser beam initially is directed at the anterior center of the mandrel (position 1). At this location the workpiece is rotated as quickly as feasible and the laser is pulsed at a very slow rate. The laser beam is slowly moved upward and angled so that the beam continually is oriented approximately perpendicularly to the workpiece surface. As the beam is moved away from the center position 1, the rate at which the laser is pulsed must be increased proportionally as the radial distance traveled by the beam increases. The laser pulse rate in the region between Numbers 1 and 2 on FIG. 1 is given by the following equation:

Laser Pulse Rate $$P = \frac{\pi r s}{30 d}$$

EQUATION 1

$d$ = distance between holes, from center to center (inches)
$p$ = pulse rate (hz)
$r$ = radial distance from axis of spin (inches)
$s$ = spin rate (rpm)

As the beam is directed at the area between Points 2 and 4 on the mandrel, the surface speed of the rotating workpiece is such that the pulse rate would become too high for good hole drilling. Thus the rotational speed of the workpiece is slowed and the pulse speed is held constant at an efficient level for drilling. At this point on the workpiece the rotary speed is determined by the following equation:

Mandrel Spin Rate $$s = \frac{30 d p}{\pi r}$$

EQUATION 2

$d$ = distance between holes, from center to center (inches)
$p$ = pulse rate (hz)
$r$ = radial distance from axis of spin (inches)
$s$ = spin rate (rpm)

Between Regions 4 and 6 the rotational speed of the workpiece is maintained at a constant, relatively high rate and the pulse rate is slowed again according to the radial distance from the center of the workpiece. Here again the Because of the presence of the holding mechanism 12 the beam directing component cannot be moved in a perpendicular orientation to the mandrel all the way to the posterior center, due to the fact that the beam directing component nozzle 16 would touch the rotating holding mechanism 12. To avoid this occurrence the nozzle is tilted slightly downwardly in such a way that the holes are drilled in an orientation spiraling inward toward the holding mechanism. The pulsing of the laser is discontinued prior to the time that the beam would strike the holding mechanism to prevent reflected energy from striking the workpiece. It is thus seen that the entire surface of workpiece 10 can be provided with blind microholes. Opening 13 is necessary in order to provide an opening in the envelope so that the same can be turned inside out during the process in which the mandrel is used to form envelopes. In this way the micro-holes can be utilized to form micropillars which ultimately form the exterior surface of the envelope. The hole at location 13 would then be closed in conventional fashion by vulcanizing a patch over the opening.

A drilling path from anterior to posterior side of the workpiece has been described for purposes of illustration. However. it will be apparent that the path can be reversed or otherwise modified. It should also be noted that: if a prosthesis is desired wherein some or all of the micropillars are not perpendicular to the surface, the laser drilling can be conducted at appropriate oblique angles to provide the desired configuration. The laser beam may also be controlled, for example, by using a longer pulse width of a lower pulse frequency to produce elongated, elliptical or oval cross-sectioned microholes. Also, while a procedure has been described wherein the workpiece is rotated in front of the laser beam. the same results can be achieved by revolving the beam around a stationary workpiece, if desired.

Figure 2:
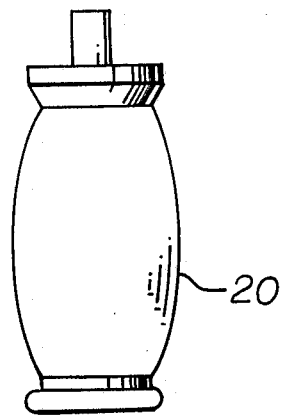
FIG. 2 is a perspective view of a bladder used in a left ventricular assist device which can be surfaced with micropillars in accordance with the invention.

FIG. 2 shows a mold 20 for a different shaped implantable device, namely a bladder for a left ventricular assist device. Micropillars can be provided on the outer surface of such a bladder using the same procedure as is described above in connection with production of prosthesis envelopes.

Figure 3:
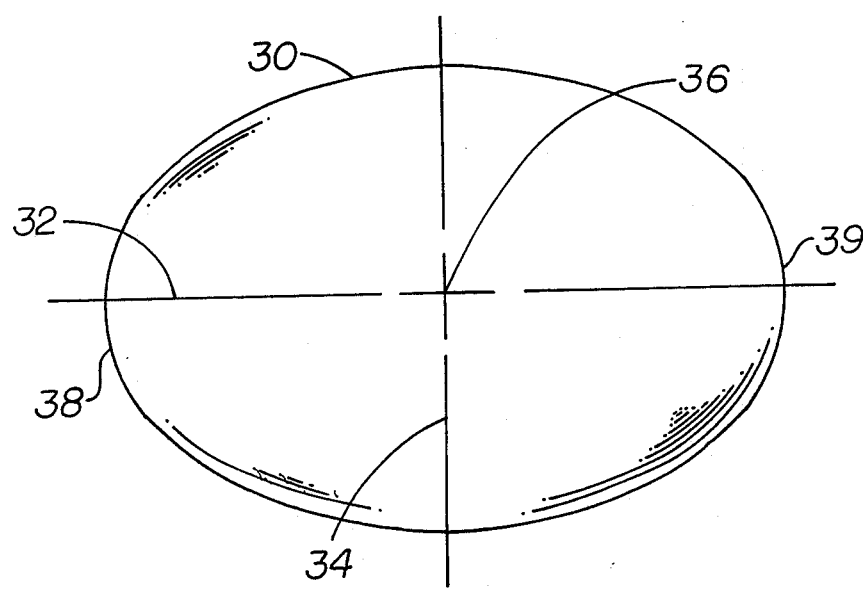
FIG. 3 is a diagrammatic top view of an eccentrically shaped mandrel.
Figure 4:
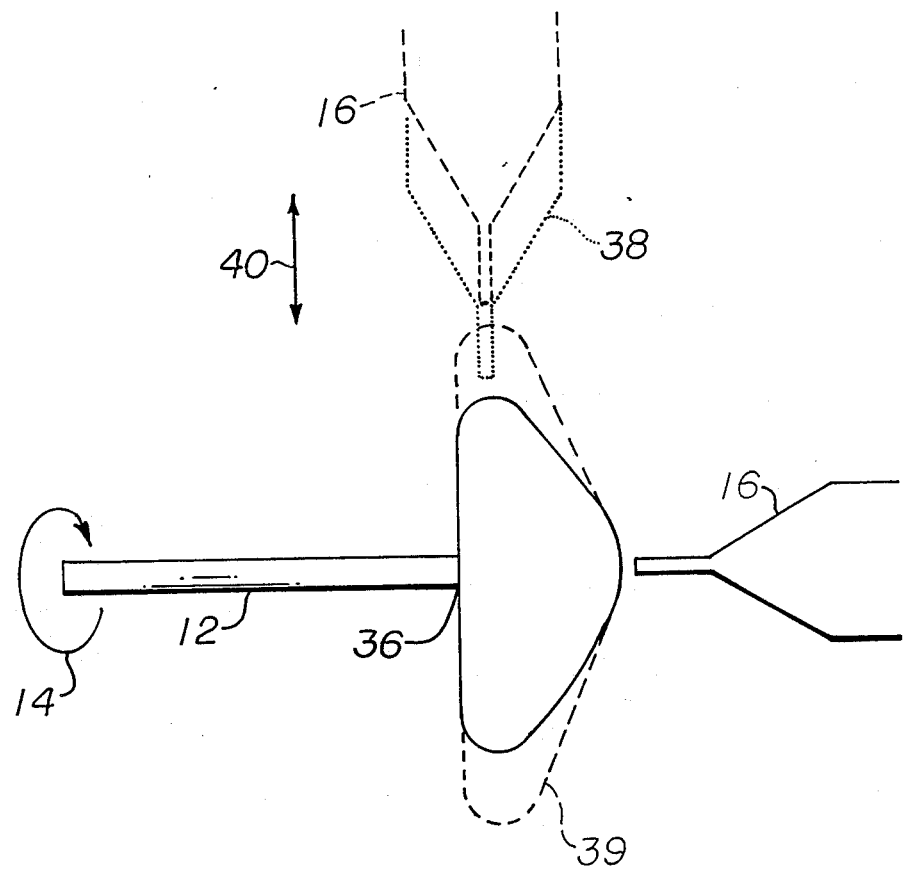
FIG. 4 is a diagrammatic view of a further embodiment of the invention, illustrating a method for forming a pattern of blind micro-holes on a non-circular object such as that of FIG. 3.

FIG. 3 is a top view of an oval or, elliptically shaped mandrel 30, which has a major axis 32 and a minor axis 34. The mandrel center 36 is at the intersection of the major and minor axes. While an elliptically shaped mandrel is shown for purposes of illustration, the process of this invention can be applied as well to other shapes, for example, a tear-drop oval shape. Such shapes are preferably mathematically describable three dimensional shapes. The mandrel is fixed for rotation about its center 36 as seen in FIG. 4. In order to form a pattern of microholes over the surface of mandrel 30 it necessary that the beam directing component be oscillated with each half revolution of the mandrel. Such oscillation to accommodate movement of apexes 38 and 39 in front of the beam directing component while maintaining an even distance between the workpiece and the beam directing component at all times. An elliptically shaped pattern corresponding to the shape of mandrel 30 is formed on all surfaces by appropriate oscillation of the beam directing component as the workpiece rotates.

The difference between the diameter of the major axis 32 and that of the minor axis 34 divided by two is a scaling factor "S" used in the calculation of the vertical or Z position of the beam directing component as the mandrel is rotated. In FIG. 4, the rotation of the mandrel is represented by dimension A. which is measured in degrees of rotation. If the laser drilling begins (i.e., A=0°) with the minor axis in the vertical (Z) position, then the following equation can be employed to calculate the appropriate point of focus for the laser optics in the Z axis:

$$Z = Z_0 + [S\ Z_0 |\sin(A)| D_m]$$

where
$Z0$ = effective drilling radius in minor axis
$D_m$ = workpiece minor diameter.

While I have described certain specific embodiments of the invention for illustrative purposes, various modifications will be apparent to those skilled in the art which do not constitute departures from the spirit and scope of the invention as defined in the appended claims.

What is claimed is:

1. A process for preparing a mandrel for forming envelopes for implantation in the human body, which envelopes are provided with micropillars on the exterior surface thereof, comprising providing a workpiece of solid stock material in the general shape of the desired envelopes, positioning said workpiece for rotation on a supporting means, moving a pulsing laser beam, directed at said rotating workpiece, around the anterior and posterior surfaces of said workpiece between a point adjacent the anterior center of rotation to a point adjacent the posterior center of rotation in a plane parallel to the axis of rotation of said workpiece while maintaining the focal point of said beam approximately at each workpiece surface at which it is directed, controlling the rate of pulsing of said laser beam and the speed of rotation of said workpiece to produce patterns of blind microholes of predetermined depth and diameter, thereby producing an array of blind microholes over substantially the entire surface of said workpiece.

2. A method according to claim 1 wherein said beam is moved radially toward and from the axis of rotation in synchronization with the revolution of said workpiece to thereby produce a pattern of microholes in a generally elliptical orientation on the surface of a workpiece which has a non-circular cross-section.

3. A method according to claim 1 wherein said beam is maintained at a n angle approximately perpendicular to said surface as it moves around said surface.

4. A process for preparing a three dimensional object provided with a pattern of blind microholes on the exterior surface thereof comprising providing a workpiece of stock material having a solid surface in the shape of the desired object, positioning said workpiece for rotation on a supporting means, moving a pulsing laser beam, directed at said workpiece, around the anterior and posterior surfaces of said workpiece in a plane parallel to the axis of rotation of said workpiece between a point adjacent the anterior center of rotation and a point adjacent the posterior center of rotation while maintaining focal point of said beam approximately at each workpiece surface at which it is directed, controlling the rate of pulsing of said laser beam and the speed of rotation of said workpiece to produce patterns of blind microholes on the substantially entire surface of said workpiece.

5. A method according to claim 4 wherein said beam is maintained in an orientation approximately perpendicular to said surface as it moves around said surface.

6. A method according to claim 4 including the steps of moving said beam radially toward and from the axis of rotation in synchronization with the revolution of said workpiece to thereby produce a pattern of microholes in a generally elliptical orientation on the surface of a workpiece which has a non-circular cross-section.

7. A process for preparing medical devices which are implantable in living tissue, which are provided with micropillars on the exterior surface thereof comprising: (a) providing a workpiece of solid stock material in the general shape of the desired implantable device, (b) positioning said workpiece for rotation on a supporting means, (c) moving a pulsing laser beam, directed at said rotating workpiece, around the anterior and posterior surfaces of said workpiece in a plane parallel to the axis of rotation of said workpiece while maintaining the focal point of said beam approximately at each workpiece surface, at which it is directed, (d) controlling the rate of pulsing of said laser beam and the speed of rotation of said workpiece to produce an array of blind microholes over the anterior and posterior surfaces of said workpiece, (e) using the resultant workpiece as a mandrel by applying to the surface thereof a dispersion of a curable elastomer, (f) curing said elastomer, and (g) removing the resultant implantable device from said mandrel.

8. A process according to claim 7 wherein said implantable device comprises an envelope for a mammary prosthesis.

* * * * *